United States Patent [19]

Malkan et al.

[11] Patent Number: 6,106,849

[45] Date of Patent: Aug. 22, 2000

[54] WATER SOLUBLE DRY FOAM PERSONAL CARE PRODUCT

[75] Inventors: Nisha Malkan, Nanuet, N.Y.; Gary Friars, Midland Park, N.J.; Robert P. Manzo, Goshen, N.Y.

[73] Assignee: Dragoco Gerberding & Co. AG, Germany

[21] Appl. No.: 09/010,246

[22] Filed: Jan. 21, 1998

[51] Int. Cl.[7] .............................. A61K 9/10; A61K 47/36
[52] U.S. Cl. .......................... 424/401; 424/485; 424/488; 510/152
[58] Field of Search .................................... 424/401, 485, 424/488; 514/777–781, 782; 428/304.4; 510/120, 130, 141, 151, 152

[56] References Cited

U.S. PATENT DOCUMENTS

| | | |
|---|---|---|
| 3,939,260 | 2/1976 | Lafon . |
| 4,292,972 | 10/1981 | Pawelchak et al. . |
| 4,789,401 | 12/1988 | Ebinger et al. . |
| 5,382,285 | 1/1995 | Morrison . |
| 5,409,703 | 4/1995 | McAnalley et al. . |
| 5,718,916 | 2/1998 | Scherr . |

*Primary Examiner*—Edward J. Webman
*Attorney, Agent, or Firm*—Pendorf & Cutliff

[57] ABSTRACT

A "single-use" personal care product designed to replace conventional single use products such as small bars of soap, mini-bottles of shampoo, etc. A water soluble foamed polymer structure, such as produced by freeze drying acemannan derived from aloe vera, serves as the carrier for the personal care active ingredient, and provides the bulk to the structure. The dry foamed product has high void volume, good dimensional stability, high surface area, dissolves easily and completely upon exposure to water and hand mechanical action, and leaves no adverse residue on the skin. The product does not require bottling or complex wrapping, and is much more economical and environmentally friendly than the conventional single use products it replaces. The product can be conveniently carried in a purse or pocket, so that a consumer need never be without his/her favorite personal care products.

4 Claims, No Drawings

WATER SOLUBLE DRY FOAM PERSONAL CARE PRODUCT

BACKGROUND OF THE INVENTION

1. Field of the Invention

The present invention concerns a "single-use" personal care product. The product can replace conventional single use products such as small bars of soap, mini-bottles of shampoo, etc. The product is storage stable while dry and contains only enough personal care cosmetic or cleansing agent for a single use. The product does not require bottling or complex wrapping, and is much more economical and environmentally friendly than the conventional single use products it replaces. The product can be conveniently carried in a purse or pocket, so that a consumer need never be without his favorite personal care products.

2. Description of the Related Art

Hotels provide their guests with small sized single use personal care products such as hand soap, shampoo, hair conditioners, body lotions, body wash products, shaving cream, etc.

One approach to providing single use products simply involves taking the same product found in large containers and simply providing a smaller volume in a smaller container. Examples of such products include shampoos, hair conditioners, skin lotions, etc., packaged in small plastic bottles. However, in practice, hotel shampoo bottles contain enough shampoo for at least two or three uses. This may be attributable to the proportionate expense of the plastic bottle, making it more reasonable commercially to simply include additional shampoo in each container, such that ultimately fewer containers need be dispensed. Used bottles must be disposed of, and usually contain some amount of unused or residual product. Hotels pay millions of dollars providing these products to guests and disposing of the waste products.

Miniaturized soap bars are another type of single use product. However, even the smallest bar of soap contains enough soap to be used for several days. These soaps must be wrapped to protect the soap from moisture. The wrapper is often inconvenient to remove, and can not be reused, such that there is no easy way to repackage a partially used bar of miniature soap for a travel kit. Thus, a partially used small soap bar is usually thrown away as soon as the guest leaves the hotel. Further, as the small soap bar shrinks with use, it becomes slippery and unmanageable, and is discarded in favor of a fresh bar. Thus, small soap bars are associated with inconvenience and waste. There is a need for improvement.

Single-dose dispensers are yet another way of providing small doses of product to a consumer. See U.S. Pat. No. 5,642,762 (laundry soap dispenser); U.S. Pat. Nos. 5,632, 418, 5,598,952, 5,507,413, 5,439,144, 5,421,489 (liquid hand soap dispensers); and U.S. Pat. No. 5,427,284 (lotion dispenser). This type dispenser is frequently found in public restrooms. There are problems associated with these product dispensers. For example, when dispensing a dose of product, some product may drip to the surface below the dispenser. This creates a slippery mess which must be cleaned up. Furthermore, unit dose product dispensers easily become clogged as liquid solidifies, or run out of product since the supply reservoir is not easy to monitor. While acceptable in public restrooms, such liquid dispensers have not been adopted in hotels.

Consumers also become accustomed to certain personal care products, or for reasons of allergy, skin conditions, etc. require a certain brand or formulation of a personal care composition. The consumer would not expect to find the favorite composition in public bathrooms, in hotels, in restaurants, etc. Thus, there is a need for a product which can be easily carried about, and which contains the specific product formulation the consumer has come to know and trust.

The laundry industry has long been providing consumers with water-soluble, single-use products. However, these products include a large amount of active ingredient, containing enough soap or conditioner for an entire load of laundry, and are designed to dissolve in large amounts of water with the prolonged agitation associated with the use of a washing machine. See U.S. Pat. No. 2,635,400 (single use soap package, termed a "soaparette," which is shaped like a cigarette and comprises a rod shell of cigarette paper wrapper containing detergent within); U.S. Pat. No. 5,055,215 (non-water soluble unit-dose dry-cleaning product); U.S. Pat. No. 4,532,063 (dissolvable bleach sheet); U.S. Pat. No. 4,938,888 (detergent sheet with alkyl polyglycoside composition); and U.S. Pat. No. 5,030,375 (powder coated laundry detergent sheet). Compressed laundry detergent pellets are also well known in the laundry detergent art. See U.S. Pat. No. 3,081,267 and U.S. Pat. No. 3,231,505 (process for making compressed detergent tablets), U.S. Pat. No. 3,172,859 (detergent briquette), U.S. Pat. No. 3,231,505 (compressed detergent and bleach tablets), U.S. Pat. No. 4,715,979 (spray-dried detergent granules compacted to form detergent pellets); U.S. Pat. No. 5,658,874 (pellets of compacted detergent granules and specific surfactants); U.S. Pat. No. 4,973,416 (liquid laundry detergent in a water-soluble packaging); U.S. Pat. No. 5,382,377 (compacted tablets containing a plasticizer or lubricant); U.S. Pat. No. 5,658,874 (detergent tablet containing a polymer which acts both as a binder and as a disintegrant); U.S. Pat. No. 4,972,017 (single use wash additive wherein the additive is coated with a water-soluble polymeric film material). The pellet, tablet, and briquette products are comprised essentially of compressed detergent, with additives imparting the needed structural integrity and dissolvability properties. Thus, while the laundry industry has become highly evolved, it provides no suggestion as to how to make single use personal care products such as shampoo or hand soap products which contain only a small amount of active ingredient, yet must be structurally sufficiently large to be easily manipulated, and which must be completely consumed in a single use, leaving no residue.

There is thus a need for a personal care product which can supply the small quantity of active ingredient needed for a single use, yet is of a sufficiently large size to be easily handled. The product should not require expensive bottling or inconvenient wrapping, and should not be associated with litter or waste products. The product should be easy to handle, must be resistant to humidity yet readily dissolvable in water, must not crumble, crack, or disintegrate upon application of mechanical forces typically associated with product manufacture, shipping, storage, and product handling, and should not leave any undesirable residue on the skin.

SUMMARY OF THE INVENTION

It is therefore an object of the present invention to provide a novel means for delivering a cosmetic or cleansing composition.

It is also an object to provide a single use personal care product which can be easily carried in a purse or pocket, and which provides the user with a preferred and known personal care composition.

Broadly, these and other objects of the present invention have been accomplished by providing a product comprising an active ingredient and a lattice forming material, wherein the active ingredient is a personal care product such as a soap, a lotion, a shampoo, a hair conditioner, etc., and wherein the lattice forming material is a dry foam-forming polymer having high void volume and high dimensional stability, yet which is easily and completely dissolvable in water and which leaves no unpleasant residue.

The polymer used in the present invention is not limited to any particular class of chemical compounds, and may be any polymer which (1) can be dried (e.g., freeze dried) to a foam to provide high void volume, such that a small amount of polymer will suffice to create a product of a size which can be easily manipulated by hand; (2) when dried and containing a cleansing or cosmetic composition, is sufficiently physically strong to withstand normal handling (i.e., does not break or chip); (3) is chemically inert to with respect to the personal care active ingredient it is compounded with; (4) preferably resists the humidity found in a normal bathroom environment; (5) readily dissolves upon exposure to water and hand mechanical action; and (6) leaves no undesirable residue on the skin.

The product is preferably produced by a process comprising mixing a small proportion of the lattice forming polymer and a small proportion of the personal care active agent in a large proportion of liquid solvent, preferably water, such that the polymer forms a dispersed phase, and drying under conditions which remove all or most of the liquid solvent, leaving a dry solid foam product which is tolerant of high-humidity environments and does not deform under mechanical stresses typically encountered in manufacturing, shipping, and storage environments and everyday handling. The product may be cut or formed into any desired shape, and can be easily formed into the shape of a small soap bar, a flower, a boat, a dove, etc. The product is completely dissolved on use, leaving behind no bulky packaging waste such as a bottle or heavy wrapper.

In a preferred embodiment, a personal care active agent such as a lotion, liquid soap, or shower gel is mixed with a hydrophilic-hygroscopic polymer, such as acemannan derived from aloe vera, after which the mixture is dispersed in a large volume of water and then freeze dried to remove the water under conditions in which the polymer forms a solid foam-like structure.

The product is completely consumed in a single ordinary use. That is, the polymer forms a stable, water soluble, high void lattice which acts as a carrier or matrix to which active agent is adsorbed, absorbed, or adhered. Only sufficient active agent is included in a single shaped product for a single use. Due to the high void volume, the foamed product is expanded to a size which makes it easy to manipulate by hand. Further, due to the high void volume, the product has a large surface area and is easily acted upon by water, such that water and hand mechanical action change the solid shape to a liquid composition.

The present invention thus provides an extremely economical and convenient "single-use" personal care product, i.e., a product that is consumed entirely when used once. The product can take the place of any of the conventional single use products such as small bars of soap, mini-bottles of shampoo, etc. The product does not require bottling or complex wrapping, contains cosmetic or cleansing agents sufficient for only a single use, and is much more economical and environmentally friendly than the conventional single use products it replaces.

Since the product is so stable, easily handled and economical, it can be carried in the purse or pocket and as such provides a "soap dispenser in the pocket". Compositions which are conventionally liquids and thus liable to leak or spill, and which one would not think of carrying in a pocket or brief case, such as vials of hair dyes or bottles of after-shave lotions, can easily be carried about in the dry formulation of the present invention without concern over risk of spilling or leaking. Further, a collection of a variety of products, such all products needed for personal care for a male for a period of a few days, can fit into a small, compact package. Further, since many personal care compositions are comprised of a small amount of active agent in a large volume of liquid vehicle, since the present invention dispenses the liquid vehicle, the present invention is much lighter and easier for a traveler to carry with him. Finally, by storing active agent in a substantially dry condition rather than a substantially liquid environment, the present invention may increase the stability of active agent during storage.

Any active agent of a personal care composition which may be substantially dried can be incorporated into the polymer foam of the present invention.

The foregoing has outlined rather broadly the features and technical advantages of the present invention in order that the detailed description of the invention that follows may be better understood. Additional features and advantages of the invention will be described hereinafter which form the subject of the claims of the invention.

DETAILED DESCRIPTION OF THE INVENTION

The present invention provides a novel delivery vehicle for single-use quantities of personal care active agents, avoiding the mess and expense of liquids in bottles, and avoiding the need to provide the large amounts of active ingredient as found in small solid soap bars.

The present invention is accomplished by providing a dry foamed personal care product comprising a personal care active ingredient and a lattice forming material, wherein the personal care active ingredient may be any conventional personal care agent such as a soap, a skin lotion, a shampoo, a hair conditioner, etc., and wherein the lattice forming material is a dry foam forming polymer having high void volume and high dimensional stability and humidity resistance, yet which is easily and completely dissolvable in water upon application of hand mechanical action, and which leaves no unpleasant residue on skin.

The product may additionally include modifiers which change the solubility properties, impart fragrance and/or color, modify feel both during dissolution and after use, and which increase or decrease dimensional stability of the product. The product may be foamed evenly, or may have a greater degree of foaming on the interior and have a lesser foamed skin or shell. The degree and distribution of foaming could be varied to meet the preferences of the user—as the degree of foaming is increased, the product has greater surface area per unit mass and thus greater solubility. A highly foamed product is also larger per unit mass, and is thus easier to handle. As the degree of foaming is reduced, the product becomes more compact and space saving. However, a produce with a reduced degree of foaming has less surface area (less wettable surface) coming into contact with water, and is thus more difficult to dissolve.

The product is preferably, and most easily, produced by a process comprising mixing the lattice forming polymer, the personal care active agent, and a solvent and drying under conditions which form a high-void-volume dry foamed product. In this way, it becomes possible to deliver the small amount of personal care composition needed for a single use in a form which is large enough to be easily handled. The polymer can be foamed such that the solid dry foam has 10 to 300 times, preferably 20 to 100 times, most preferably 25 to 50 times the volume of the non-foamed liquid polymer and personal care active agent mixture.

In a preferred embodiment of the invention, the polymer is acemannan derived from Aloe vera. Aloe vera has been used for over 2,000 years for a number of remedial applications, including topical application for treatment of sunburn, hemorrhoids, itching, blistering, skin blemishes, jellyfish bites, etc. Thus, an Aloe vera derived polymer is preferred as the carrier in that it contributes a synergistic improvement to a personal care composition. This is important, in that the carrier may comprise up to 98% by weight of the total personal care product.

The foamed product can be shaped while foaming, such as by foaming in a mold, or can be cut or shaped after foaming. The foamed product can be printed with logos, information or symbols, such as labeling a particular product as a shampoo or after-shave lotion. However, considering the intended use as a personal care product, it is preferred that the amount of ink, if any, be small and/or the ink be a non-staining type such that the ink leaves no coloration on the hand or hair (unless, of course, the personal care product is intended to be a hair coloring product).

The individual components blended to a mixture for foaming and drying (e.g., freeze drying) for forming the foamed solid product, the process of forming the product, and various products produced in accordance with the invention will now be discussed in greater detail.

Personal Care Active Ingredient

The personal care active ingredients may be any of those used in the industry. Most such personal care active agents are solids or can be dried to solids, yet are emulsified or suspended in solids in order to be applied to the body in liquid form or in a liquid environment. Any of these personal care active agents which are available as liquids but can be dried to solid or semi-solid form can be easily used in the present invention and are preferred in that they are easily dissolved in the solvent and polymer in the process of making the product of the present invention. However, active agents which do not dry to a solid or semi-solid, but which do not interfere with the lattice of the foam forming polymer, can also be used in the present invention.

The active agent prior to being incorporated into the carrier may have a variety of physical forms which include, but are not limited to: liquid, gel, cream or other semisolid, solid, powder or even gas (e.g., aromatic compounds). The active ingredient is preferably in the form of a liquid, such as a liquid hand soap, in which form it is easily mixed with the polymer and solvent. Active agent compositions which are preferred can be easily selected when considering the concept of the present invention. That is, the present final product is provided in the form of dry foam, but must be easily converted by water and hand mechanical action to a liquid form. Thus, the personal care active ingredient may be any shampoo, skin moisturizing composition, soap, hair color composition, insect repellent, etc., which can be substantially dried when forming the foamed product, yet which is easily solubilized in water to form a liquid or gel composition.

Additionally, some or all of the active ingredients may be encapsulated into small or microscopic "beads" or enclosures using any technique commonly used for chemical encapsulation. It will be recognized that volatile substances such as fragrance chemicals, particularly when encapsulated, may be mixed or combined with various solvents, diluents, or other substances which act to dissolve the fragrance chemicals or alter their intensity, stability, viscosity, rate of release or other physical or chemical characteristics.

Specific personal care active agents are well known and easily selected by those working in the art, are too numerous to discuss individually herein, and thus for economy are best described herein by reference to patents which teach them in detail. Examples include of personal care product active agents include:

liquid shampoo compositions, including combination shampoo and conditioner compositions, as disclosed in U.S. Pat. Nos. 4,364,837; 5,612,024; 5,612,301; 5,573,709; 5,536,493; 5,409,628; RE 34,584; 5,246,694; 5,198,209; 5,154,847; 5,152,914; 5,151,210; 5,100,657; 5,034,218; 4,927,563; 4,788,006; 4,741,855; 4,704,272 and 4,676,978;

liquid soaps, preferably liquid hand soaps, as disclosed in U.S. Pat. Nos. 5,518,733; 5,356,803; 5,266,690; 5,154,849; 5,041,236; 4,678,606 and 4,617,148;

liquid hair dyes as disclosed in U.S. Pat. Nos. 5,686,066; 5,645,610; 5,637,115; 5,635,461; 5,597,386; 5,542,953; 5,534,037; 5,529,583; 5,516,916; 5,468,256; 5,421,833; 5,409,502; 5,344,463 and 5,318,599;

liquid hair conditione r compositions as disclosed in U.S. Pat. Nos. 5,344,643; 5,334,376; 5,332,569; 5,270,035; 5,213,793; 5,472,688; 5,100,657; 5,085,857 and 5,085,857;

liquid skin lotions as disclosed in U.S. Pat. Nos. 5,589,515; 5,552,158; 5,232,693; 5,227,242; 5,358,752; 5,221,533; 4,655,232, 104,341,799; 4,285,973 and 4,272,519;

anti-acne lotions as disclosed in U.S. Pat. Nos. 5,621,006; 4,255,418; 5,470,884; 4,545,990; 4,505,924; 4,213,978; 4,548,942; 4,446,145; 5,409,917; 5,122,519 and 4,486,448;

liquid sunscreens and tanning oils as disclosed in U.S. Pat. Nos. 4,193,989; 5,575,988 (combined sunscreen and insect repellent); U.S. Pat. Nos. 5,209,923; 5,670,139; 5,665,781; 5,648,398; 5,635,174; 5,633,236; 5,621,013; 5,589,195; 5,556,881 and 5,521,165;

men's and ladies after-shave lotions as disclosed in U.S. Pat. Nos. 5,665,339; 5,527,530; 5,449,512 and 5,120,709;

and other compositions such as insect repellent compositions as disclosed in U.S. Pat. No. 5,206,022; diaper rash lotions as disclosed in U.S. Pat. Nos. 5,525,346 and 5,436,007; hair restorer compositions as disclosed in U.S. Pat. No. 5,494,667; hair straightener compositions as disclosed in U.S. Pat. No. 5,679,327; and topical anti-microbial agents such as antirhinovirus agents as disclosed in U.S. Pat. No. 4,738,984.

Polymer

The polymer used in the present invention is not limited to any particular class of chemical compounds, and may be any polymer which (1) can be dried (e.g., freeze dried) to a foam to provide high void volume, such that a small amount of polymer will suffice to create a product of a size which can be easily manipulated by hand; (2) when dried and containing a cleansing or cosmetic composition, is sufficiently physically strong to withstand normal handling (i.e., does not break or chip); (3) is chemically inert to with respect to the personal care active ingredient it is compounded with; (4) preferably resists the humidity found in a normal bathroom environment; (5) readily dissolves upon exposure to water and hand mechanical action; and (6) leaves no undesirable residue on the skin.

The polymers are preferably hydrophilic and hygroscopic, and examples of hydrophilic-hygroscopic polymers include both unmodified and modified derivatives of polymeric carbohydrates.

Suitable polymeric carbohydrates include polysaccharides such as acemannan, konjac mannan (a glucomannan), guar gum (a galactomannan), heparin (an acid mucopolysaccharide), glucan and their modified analogs and derivatives. A variety of additional polysaccharides and/or their derivatives, modified or unmodified, may potentially be used as a base material for the dried polymeric saccharide solid foam, includeing alginates, carrageenan, chitin, ficoll, fructans, galactans, hydrophilic cellulose derivative, dextrans, glycogen, maltans, starch, glycosaminoglycans, gum arabic, karaya gum, lentinan, mannans, pectins, lipopolysaccharides, proteoglycans, proteochondroitin sulfates, sepharose, xylans, muramic acids, neuraminic acids, sialic acids, uronic acids, etc. Any of these polymers may be used so long as they satisfy, or are chemically modified to satisfy, the above requirements.

In a preferred embodiment of the invention, the polymer is acemannan derived from Aloe vera. The composition and manner of action of aloe vera is not fully understood. It has been reported that steroids and wound healing hormones may be contained in aloe vera, but it is more commonly believed that the moisturizing emollient and healing properties of aloe vera are due to the polysaccharides present, or to synergistic effects of the polysaccharides and other substances present in the gel. Leun, A.; Effective Ingredients of Aloe Vera, Drugs & Cosmetics, June 1977, pp. 34–5 and 154–5.

Aloe vera is known to have anti-bacterial properties, as disclosed by Lorenzetti, et. al., J. Pharm. Sci. 53, 1287 (1964). A list of species of aloe which have therapeutic value can be found in U.S. Pat. No. 4,646,029 (Grollier et al), the entire text of which is incorporated herein by reference. U.S. Pat. No. 4,481,185 (Grollier et al) mentions the anti-sunburn properties of aloes juices in column 4. U.S. Pat. No. 4,788,007 (Baron) teaches UV absorption properties of aloe, and teaches the use of aloe gel as liquid sunglasses applied topically in the eyes. U.S. Pat. No. 4,857,328 (Trenzeluk) teaches an anti-burn mixture containing aloe, petroleum (Example 1) and cetyl alcohol (Example 3). U.S. Pat. No. 5,118,673 (Carpenter et al) provides an extensive discussion of the history, biological properties, and pharmacy of aloe products, the entire text of which is incorporated herein by reference. Carpenter et al discuss rapid healing of radiation burns with aloe vera gel in column 7, line 39.

Techniques are well known to those in this art of modifying solubility characteristics, mechanical strength, moisture and humiditity resistance, etc. of foamed polymers.

These hydrophilic-hygroscopic polymers, such as polymeric carbohydrates, can form hydrogels when dispersed as a colloid in a liquid medium, such as water. A hydrogel, as used herein, is a colloid in which the polymer molecules or particles are in the external or dispersion phase and a liquid medium in the internal or dispersed phase. Hydrogels are complex lattices in which the dispersion media are trapped rather like water in a molecular sponge. Depending on the amount of the liquid medium present, the consistency of hydrogel can vary. Usually, the more liquid the medium is, the less viscous is the hydrogel.

Under certain conditions, a hydrogel of a polymeric carbohydrate may be dried without totally collapsing the arrangement or lattice of dispersed polymeric carbohydrate particles. For example, freeze-drying or lyophilizing, which involves the rapid freezing of a hydrogel at a very low temperature followed by a "drying" by sublimation in a high vacuum, gives a solid, yet flexible, polymeric carbohydrate foam.

Foaming may also be accomplished by resort to other techniques, such as blending air into a composition using a blender or high speed mixer, by expanding using an aerosol followed by drying. However, for speed and consistency, freeze drying is preferred.

The solid foam material is in a lightweight cellular form having gas (air) bubbles dispersed throughout. In this physical solid foam form, a dried hydrogel serves as a carrier for the cosmetic or cleansing compositions which are "trapped" within its interstices.

Polar Solvent

The polar solvent may be any suitable solvent, but for economic and ecological reasons, the solvent is preferably water. The water can be pure water or may contain small amounts (e.g., less than 1%) of antimicrobial agent, wetting agent, preservative, UV-absorber, or other ingredient conventionally employed in the cosmetic art.

Coloring Agent

A coloring agent, preferably a water-soluble coloring agent, may be added to the water phase for imparting color to the final product, and examples of colorants include Food, Drug and Cosmetic Agency approved colors. Colored foams can be used to generate colored shapes such as flowers. It is generally preferred to use small amounts of dyes, and to use dyes which do not react with skin or hair.

Alternatively, it is also possible in accordance with the present invention to incorporate products such as hair dyes, hair lighteners, etc. into the foam carrier.

Fragrance

Fragrance may be a part of the cosmetic or cleansing composition added to the lattice polymer, or fragrance compounds may be added to impart fragrance to non-fragrant cosmetic or cleansing compositions or to enhance or modify weakly fragrant cosmetic or cleansing compositions. If added, substances used to produce a desired fragrance may be any one or more of those which are commonly used by those skilled in the art of toiletry fragrance chemistry or perfumery, some of which are listed in the following texts: Robert R. Calkin, J. Stephan Jellinek, *Perfumery, Practice and Principle*, John Wiley and Sons, Inc., New York, 1994; Rudiger Hall, Dieter Klemme, Jurgen Nienhaus, *Guide to Fragrance Ingredients*, H&R Edition, R. Gross & Co. Publishing, Hamburg, 1985; Julia Muller, *The H&R Book of Perfume*, H&R Edition, Johnson Publications, Ltd., London, 1984; *Fragrance Guide-Feminine Notes, Masculine Notes*, H&R Edition, R. Gross & Co. Publishing, Hamburg, 1985 which are incorporated by reference herein. It is specifically intended that the present invention not be limited to any particular fragrance or combination of fragrances, whether known or discovered in the future since any fragrance or chemical substances which humans find pleasant and desirable to inhale are within the scope of the present invention.

The amount of fragrance substance (e.g., perfume base) included in the composition may vary, and the amount of the fragrance substance may comprise from 0.01 to 10% by weight of the total cosmetic or cleansing composition, with about 0.5% to about 1% being preferred. Quantities of fragrance outside of this preferred range may also be used, as well as significantly larger amounts.

Process of Manufacture

Processes for freeze drying of hydrogels to form solid foams are well known and are described, for example, in U.S. Pat. No. 5,409,703, the entirety of which is incorporated herein by reference.

Acemannan is one example of a carbohydrate polymer that can be formed into this solid foam of dried hydrogel. Acemannan is an active substance of the aloe plant, and has been shown to relieve pain and optimize healing. U.S. Pat. No. 5,409,703 (Carpenter et al) provides an extensive discussion of the history, biological properties, and pharmacology of aloe products, the entire text of which is incorporated herein by reference. Reference may also be made to U.S. Pat. No. 5,387,415 which discloses aloe vera pellets and a process for making these pellets which comprises mixing aloe vera juice, defined to include native juice obtained directly from the leaf or to include either filtered or cleaned juice or redissolved juice from dry extract, with a hydrophilic protein macromolecule to act as a carrier, and freeze-drying the mixture to form solid pellets. This patent is directed to storage and transporting of aloe vera, and is not concerned with a foamed aloe product containing cleansing or cosmetic compositions.

Product

The product is characterized by being resistant to normal environmental influences such as humidity, room temperature, and mechanical forces, yet is readily solubilized on addition of small quantities of water under application of hand mechanical action. The product may be solubilized after first passing through a gel phase, which may have benificial properties in the case of skin cream compositions or moisturizers.

The dried hydrogel of a hydrophilic-hygroscopic polymer in a solid foam physical state can be cut or formed to almost any shape suitable to an end user—for example, the shape of a ship or a duck for use in a bathtub, the shape of a flower for a cosmetic composition, the shape of a bottle or container, etc. The foam-like nature of the composition lends itself to being easily shaped and molded, although the product may also be shaped to desired form during the process of forming the foam.

Due to the inertness of the product to normal environmental conditions, the product does not require a separate wrapping or packaging (though there is no restriction to wrapping or packaging the product if desired). This feature can help keep manufacturing and storage costs down, and is environment-friendly.

The product comprising a solid foam polymer of the present invention can be used with soaps, shaving creams, lotions, shampoos, hair conditioners and protein treatments, hair straightening agents, hair perming agents, mild facial cleansing systems, face masks, anti-bacterial cleansing systems, specialized baby care products, shampoos, shower gels, bath additive products, face and body washes, household cleaning products, disinfectants, laundry detergents, laundry enzymes, and even fabric softeners.

The main ingredients in the final product are the personal care active ingredient and the foam forming polymer. The proportions of these ingredients varies with the mechanical strength of the respective active ingredient and polymer, with proportions ranging from 10:1 to 1:10 active ingredient to polymer, preferably 2:1 to 1:10 active ingredient to polymer, most preferably 1:1 to 1:5 active ingredient to polymer. The final dried foamed product may contain from 1 to about 15% solvent (e.g., water), and preferably contains about 5 to 10% water.

EXAMPLE 1

Single Use Dry Foam Shampoo Dry Foamed Product

Unless indicated to the contrary, all "parts" referred to herein are "parts by weight".

Polysaccharide dispersion: One liter of water is adjusted to pH 6–6.5 with sodium hydroxide at room temperature. To this liter is added 1.5 gram of dry acemannan powder with mixing until fully dispersed to yield a colloidal dispersion (hydrocolloid).

Liquid shampoo: To 54.75 parts water are added 25.00 parts Standapol AHV (ammonium lauryl sulfate) supplied by Henkel, 15.40 parts Stanapol EA-1 (ammonium lauryl ether sulfate) supplied by Henkel, 2.50 parts Standamid KD (cocamide DEA) supplied by Henkel, 1.33 parts citric acid, 40% aqueous, supplied by Henkel, 0.02 parts Kathon CG supplied by Rohm and Haas, and 1.00 parts ammonium chloride, 25%. aqueous. The ingredients are mixed to form a clear liquid shampoo.

To the polysaccharide dispersion is added 1 ml of the liquid shampoo with mixing, to provide a shampoo to polymer mixture in a ratio of approximately 1:3. This mixture is freeze dried as described in U.S. Pat. No. 5,409,703, the entirety of which is incorporated herein by reference, to produce a dry solid foam. The foam is off-white, has good mechanical strength, and resists humidity.

The foam is easily trimmed into the shape of a small disk and is tested by asking subjects to shampoo their hair. In each case the shampoo bar completely dissolves under the conditions of normal shampooing, the subjects being able to wash their hair without requiring any instruction, with the hair feeling and smelling clean with no residue.

EXAMPLE 2

Single Use Hair Conditioner Dry Foamed Product

Polysaccharide dispersion: The same polysaccharide as prepared in Example 1 is used in this Example.

Hair Conditioner: To 93.21 parts deionized water are added 1.5 parts Natrasol 250 HHR (hydroxyethyl cellulose) supplied by Aqualon, 1.0 part Crodacol C-70 (cetyl alcohol) supplied by Croda, 1.5 parts Quaternium—18 supplied by Witco, 0.8 parts Incromine SB (Stearamidopropyldimethylamine) supplied by Croda, 1.0 part 7224 Fluid (trimethylsilylamodimethicone and octoxynol 40 and isolaureth-6 and propylene glycol) supplied by Dow Corning, 0.5 parts Kathon CG supplied by Rohm and Haas, and 0.49 parts citric acid, 40%.

To the polysaccharide dispersion is added 10 ml of the liquid hair conditioner to provide a mixture with a hair conditioner to polysaccharide dry weight ratio of about 1:2. The mixture is foamed by freeze drying as in Example 1 to form a dry foamed hair conditioner product.

The foam is easily trimmed into the shape of a small bar and is tested by asking subjects to condition their hair after washing their hair. In each case the conditioner completely dissolves under the conditions of normal hair conditioning, the subjects being able to condition their hair without requiring any instruction. Once dried, the hair feels clean and controllable.

EXAMPLE 3

Single Use Hand and Body Cleansing Dry Foamed Product

Polysaccharide dispersion: The same polysaccharide as prepared in Example 1 is used in this Example.

Hand and Body Lotion: To 78.8 parts deionized water are added 0.1 part Germall 115 (imidazolidinyl urea) supplied by Sutton, 0.1 parts methyl paraben supplied by TRI-K, 0.2 parts Carbopol 934 (Carbomer 934) supplied by B. F. Goodrich, 0.2 parts Tween 20 (polysorbate 20) supplied by ICI, and 5.0 parts glycerin. These ingredients are well mixed, and to this mixture is added 2.0 parts Kessco Glycerol Monostearate (Glyceryl Stearate) supplied by Stepan, 0.5 parts Emery 1740 (Lanolin) supplied by Henkel, 5.8 parts Mineral Oil (90 CS) supplied by Protameen, 2.0 parts Protachem MLD (Glyceryl Laurate) supplied by Henkel, 3.0 parts Emersol 132 (stearic acid U.S.P.) supplied by TRI-K, 0.2 parts propyl paraben supplied by Dow Corning, and 0.1 parts Dow Corning 200 Fluid (Dimethicone—100 CS) supplied by Dow Corning. These ingredients are well mixed, and 1.0 part triethanolamine 99% supplied by Union Carbide and 1.0 part Dragosantol® supplied by Dragoco were added. Fragrance was added to make 100 parts total. The product was a liquid hand and body lotion.

To the polysaccharide dispersion is added 2.5 ml of the liquid hand and body lotion to provide a mixture with a hand and body lotion to polysaccharide dry weight ratio of about 1:3. The mixture is foamed by freeze drying as in Example 1 to form a dry foamed hand and body cleansing product.

The foam is easily trimmed into the shape of a small bar and is tested by asking subjects to wash their hands. In each case the foamed product completely dissolves under the conditions of normal hand washing, the subjects being able to clean their hands without requiring any instruction. Once dried, the hands feel and smell clean.

EXAMPLE 4

Single Use Sunscreen Dry Foamed Product

Polysaccharide dispersion: The same polysaccharide as prepared in Example 1 is used in this Example.

Waterproof Sunscreen Composition: To 72.75 parts deionized water are added 10.0 parts hydroxypropyl methylcellulose supplied by Dow Chemical, 0.15 parts Quaternium—15 supplied by Dow Chemical, 0.05 parts disodium EDTA supplied by Hampshire. To this mixture is added 7.0 parts octyl methoxycinnimate supplied by Givaudan, 3.0 parts octyl salicylate supplied by BASF, 2.0 parts oxybenzone supplied by BASF, and C12–C15 alcohol benzoate supplied by Finetex. Then, 0.25 parts acrylates (C10–C30 alkyl acrylate crosspolymer) supplied by B. F. Goodrich, 0.2 parts Carbomer 954 supplied by B. F. Goodrich, 0.15 parts methylparaben supplied by Protameen and 0.05 parts propylparaben supplied by Protameen are added. Then, 0.4 parts triethanolamine, 99%, supplied by Union Carbide and fragrance to make 100 parts are added.

To the polysacaharide dispersion is added 2.5 ml of the sunscreen composition to provide a mixture with a sunscreen composition to polysaccharide dry weight ratio of about 1:3. The mixture is foamed by freeze drying as in Example 1 to form a dry sunscreen composition containing foamed product.

The foam is easily trimmed into the shape of a small bar and is tested by asking subjects to rub the bar with water in the palm of one hand until the bar turns to gel, and then rubbing the gel over their arms and face. In each case the foamed product completely dissolves to form a gel, and the gel was easily applied to the arms and face to provide a sunscreen.

EXAMPLE 5

Single Use Hand Soap Dry Foamed Product

Polysaccharide dispersion: The same polysaccharide as prepared in Example 1 is used in this Example.

Liquid Hand Soap: To 39 parts deionized water are added 28 parts Standapol WAQ-LC (Sodium Lauryl Sulfate) supplied by Hinkel, 5.0 parts Velvatex BA-35 (Cocamidopropyl Betaine) supplied by Hinkel, 3.0 parts Standamid SD (Cocamide DEA) supplied by Hinkel, 1.5 parts Cetiol HE (PEG-7 Glycryl Cocoate) supplied by Hinkel, 1.0 sodium chloride, 0.5 parts Germaben II-E supplied by Sutton, 0.5 parts fragrance, supplied by Dragoco, 0.1 part Versenol 120 (Trisodium HEDTA) supplied by Dow Chemical, and 0.5 part Dragosantol® supplied by Dragoco. The ingredients were mixed well, and the pH of the mixture was adjusted to pH 5.5–6.0 by addition of a 50% aqueous solution of citric acid. The product was a liquid hand soap.

To the polysaccharide dispersion is added 0.25 ml of the liquid hand soap to provide a mixture with a hand soap to polysaccharide dry weight ratio of about 1:30. The mixture is foamed by freeze drying as in Example 1 to form a dry foamed hand soap.

The foam is easily trimmed into the shape of a small bar and is tested by asking subjects to wash their hands. In each case the foamed product completely dissolves under the conditions of normal hand washing, lathers, the subjects being able to clean their hands without requiring any instruction. Once dried, the hands feel and smell clean.

ADDITIONAL EXAMPLES

Additional Examples are carried out by variously substituting konjac mannan, guar gum, and glucan for acemannan as the foam forming polymer, and by substituting "off the shelf" liquid hand soaps, liquid body lotions, shaving creams, hair protein treatments, hair straightening agents, hair perming agents, mild facial cleansing systems, face mask compositions, anti-bacterial cleansing systems, specialized baby care products with anti-rash ingredients, and bathwater additive products in place of the above illustrated active ingredients. Similar results are obtained.

Although this invention has been described in its preferred form with a certain degree of particularity with respect to a solid foam product comprising a hydrophilic-hygroscopic hydrogel polymer which contains within its matrices various hand soap cleansing compositions, it is understood that the present disclosure of the preferred form has been made only by way of example, and that numerous changes in the details of structures and composition of the product may be resorted to without departing from the spirit and scope of the invention.

What is claimed is:

1. A dry foamed personal cleansing product comprising:
   a water soluble hygopcopic dry foamed polymeric carbohydrate matrix, and
   a personal cleansing active ingredient dispersed in said polymeric carbohydrate matrix, wherein said personal cleansing active ingredient is selected from the group consisting of hand soap, shampoo, body wash products, shaving cream, bubble bath, bath gel, and after-shave lotions,
   wherein said dry foamed polymeric carbohydrate matrix is produced by dispersing said polymeric carbohydrate in a solvent and freeze drying, and
   wherein said polymeric carbohydrate is selected from the group consisting of polysaccharides, glucomannan, galactomannan, acid mucopoly-saccharides, glucan, modified glucan analogs and derivatives, alginates, carrageenan, chitin, ficoll, fructans, galactans, hydrophilic cellulose derivatives, dextrans, glycogen, maltans, starch, glycosaminoglycans, gum arabic, karaya gum, lentinan, mannans, pectins, lipopolysaccharides, proteoglycans, proteochondroitin sulfates, sepharose, xylans, muramic acids, neuraminic acids, sialic acids, and uronic acids.

2. A dry foamed personal care product comprising:
   a water soluble dry foamed polymeric carbohydrate matrix, and
   a personal care active ingredient dispersed in said polymeric carbohydrate matrix,
   wherein said personal care active ingredient is selected from the group consisting of hand soap, shampoo, hair conditioners, face and body lotions, body wash products, sun-tan lotions, shaving cream, bubble bath, bath gel, facial lotions, and after-shave lotions,
   wherein said foamed dry polymer is produced by dispersing said polymeric carbohydrate in a solvent and freeze drying, and
   wherein said polymeric carbohydrate is selected from the group consisting of acemannan, konjac, mannan and heparin.

3. A dry foamed personal care product comprising:
   a water soluble dry foamed polymeric carbohydrate matrix, and
   a personal care active ingredient dispersed in said polymeric carbohydrate matrix,
   wherein said personal care active ingredient is selected from the group consisting of hand soap, shampoo, body wash products, shaving cream, bubble bath, bath gel, facial lotions, and after-shave lotions, and
   wherein said polymeric carbohydrate is acemannan.

4. A dry foamed personal care product, wherein said product is formed by a process comuprising:
   (a) mixing 0.01 to 10.0 wt % of a carbohydrate polymer and 0.01 to 5.0 wt % of a personal care active ingredient selected from the group consisting of hand soap, shampoo, hair conditioners, face and body lotions, body wash products, sun-tan lotions, shaving cream, bubble bath, bath gel, facial lotions, shaving cream, and after-shave lotions in 99.98 to 90 wt % water to form a colloidal dispersion; and
   (b) drying said dispersion under conditions to form a dry foamed product having 40 to 99% voids by volume, and
   wherein said personal care active ingredient is selected from the group consisting of hand soap, shampoo, hair conditioners, face and body lotions, body wash products, sun-tan lotions, shaving cream, bubble bath, bath gel, facial lotions, shaving cream, and after-shave lotions;
   wherein said polymer is acemannan;
   wherein said personal care product is at least 2 cm$^3$; and
   wherein the proportion of personal care active ingredient to foamed polymer is from 1:50 to 1:10.

* * * * *